United States Patent [19]

Barberet et al.

[11] Patent Number: Plant 7,185

[45] Date of Patent: Mar. 6, 1990

[54] CARNATION NAMED LONRIAKEN

[75] Inventors: Nicole Barberet; Henri Blanc, both of Antibes, France; Antonio Di Giorgio; Renato Di Giorgio, both of San Remo, Italy

[73] Assignee: Etablissements Barberet et Blanc, La Londe-Les-Maures, France

[21] Appl. No.: 315,544

[22] Filed: Feb. 27, 1989

[51] Int. Cl.[4] ..... A01H 5/00

[52] U.S. Cl. ..... Plt./73

[58] Field of Search ..... Plt./73

*Primary Examiner*—James R. Feyrer

*Attorney, Agent, or Firm*—Charles W. Rummler

[57] ABSTRACT

A new and distinct standard carnation cultivar particularly distinguished by its profuse production of medium sized blooms having a uniform dark red coloration, borne singly on long, strong, upright stems, the plant reaching a height of about 150 cm. at eight months of growth, and having a recurrent blooming habit with moderately abundant foliage.

1 Drawing Sheet

BACKGROUND OF THE NEW PLANT

This new carnation cultivar originated as a seedling of a hybrid developed in 1985 at the nursery maintained by Antonio and Renato Di Giorgio by crossing two varieties selected from their collection of carnations maintained at their nursery for breeding purposes, this particular seedling, having been selected by us for propagation because of its profuse production of medium sized flowers of a uniform dark red coloration borne on the strong, upright stems of a very tall plant having a height of about 150 cm, at eight months of growth. Because of its apparently very stable growth habit well suited to commercial propagation, this seedling was propagated at our direction by means of cuttings at San Remo with such satisfactory results that we directed that such propagation be continued through several successive generations and this proved to us that novel characteristics of this seedling would hold true from generation to generation and that its homogeneity could be assured for large-scale commercial use of the new plant.

Accordingly, our new carnation variety is now being propagated for commercial purposes by means of cuttings, as well as by in vitro propagation procedures, at Establissments Barberet et Blanc, Laboratoire de Physiologie Vegetale, 83250 La Londe-Les Maures, France.

DESCRIPTION OF THE DRAWING

Our new carnation variety is illustrated by the accompanying photographic drawing, which shows several blooming stems with flowers and buds in several stages of development, the color rendition being as nearly true to that herein specified as is reasonably possible to obtain by professional photographic procedures.

DESCRIPTION OF THE NEW PLANT

The following is a detailed description of our new carnation variety based upon observations made in the Spring of 1988 of plants grown in greenhouse, as well as outside, at San Remo, Italy, the color designations stated herein being according to The R.H.S. Colour Chart published by The Royal Horticultural Society of London, England.

THE PLANT

Origin: Seedling.

Parentage:

- Seed parent.—Variety No. 64.
- Pollen parent.—Variety No. 291.
  - Both parents are unpatented and unnamed and are identified in the breeding records maintained in the Di Giorgio nursery office at Via Villetta 41, 18038 San Remo, Italy.

Classification:

- *Botanic.—Dianthus caryophyllus.*
- *Commercial.*—Standard Carnation.

Form: A tall, erect bush having at least four stems emitted near the ground.

Height: Averages about 150 cm. at eight months of growth.

Main stem length: Less than 15 cm. due to pinching to foster branching.

Branching: This plant is well branched.

Growth: Vigorous, upright and rapid.

Foliage:

- *Quantity.*—Moderately abundant.
- *Number of leaves.*—More than 120.
- *Leaf size.*—(At the seventh node) About 17 cm. long and 0.9 cm. wide.
- *Leaf shape.*—Linear — With acuminate apex and entire upwardly curved margins.
- *Texture.*—Leathery.
- *Color.*—Both upper and under sides, 189-A/B.

THE BUD

Size: Large.

- *Diameter.*—Averages about 2.3 cm.
- *Length.*—Averages about 3.6 cm.

Shape: Ovoid, before sepals divide.

Rate of opening: Normal.

Color of petals: When sepals first divide and petals begin to unfurl: the same as at full bloom.

Sepals:

- *Number.*—Five.
- *Shape.*—Generally ovoid, with acuminate tip and joined together at the lower parts.
- *Character.*—The sepals are hooded over the bud before they divide and stand up when the flower opens.

*Color.*—Inside, 145-B and 185-C. Outside, 137-C and 145-B.

*Striae.*—Longitudinal.

Calyx:

*Shape.*—Bell-shaped.

*Size.*—Large.

*Aspect.*—Smooth.

*Splitting.*—Sometimes a little splitting occurs.

Flower stem:

*Length.*—Averages about 73.6 cm., when cut at the tenth node.

*Character.*—Rigid and erect.

*Color.*—189-A/B.

THE FLOWER

Blooming habit: Recurrent, blooming profusely in the Spring, Midseason and Fall blooming periods with a tendency, however, to give few blooms in the Fall.

Size of flower: Medium.

*Diameter.*—Averages about 7.6 cm.

*Depth.*—Averages about 5.6 cm.

Borne: Singly on a long, strong, upright stem.

Shape: When bloom first opens, high-centered. When bloom matures, dome-shaped.

Petalage:

*Number of Petals.*—Averages about sixty-five.

*Arrangement.*—Imbricated.

*Form.*—Fan-shaped with serrated outer end margins.

*Texture.*—Leathery.

*Aspect.*—Satiny.

*Color.*—Both inner and outer petals: Body — dark red, 45-A/B. Base — Greenish. Reverse side — blood red, 45-D.

Petaloids:

*Number.*—Less than eight.

*Size.*—Smaller than the petals.

*Color.*—The same as the petals.

Flower stem:

*Character.*—Upright with good strength and outwardly curving foliage.

Discoloration after full bloom: A little.

Persistence: The flower petals hang on and dry.

Fragrance: Perceptible.

Lasting quality: As a cut flower, at least ten days in vase keeping.

REPRODUCTIVE ORGANS

Stamens:

*Number.*—Varies from ten to twenty.

*Arrangement.*—Encircling the ovary.

*Anthers.*—Size: Less than 4 mm. Color: A little reddish.

*Filaments.*—Length: Average about 2.3 cm. Color: A little reddish.

Pistils:

*Number.*—Three or four.

*Styles.*—Length: About 2.3 cm. Color: Reddish.

*Stigma.*—Color: Reddish.

Character of ovaries: Ribbed.

This carnation variety most nearly resembles the variety Ember (unpatented). Our new variety, however, differs from Ember by having a more serrated flower petal.

We claim:

1. A new and distinct standard variety of carnation plant substantially as herein shown and described, particularly characterized by its profuse production of bright red blooms of medium size borne on long, strong, upright stems of a vigorous, rapidly growing and tall plant having moderately abundant foliage.

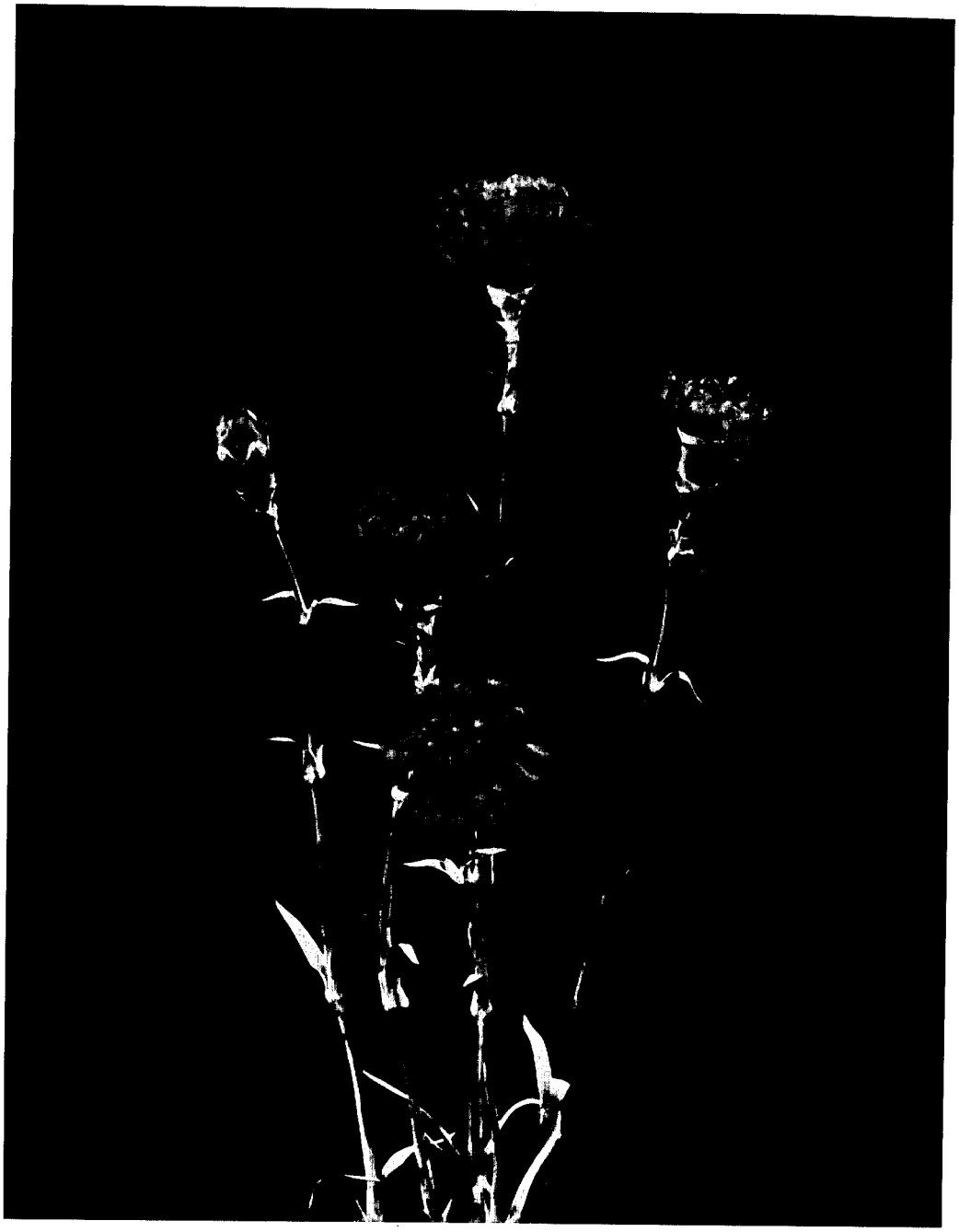

* * * * *